United States Patent [19]

Voelskow et al.

[11] 4,121,524

[45] Oct. 24, 1978

[54] METHOD OF AND APPARATUS FOR TREATING REFUSE

[75] Inventors: Peter Voelskow, Bad Kreuznach; Horst Rother, Berlin; Gustav Schlotterer, Dusseldorf; Hermann Pfeiffer, Eschenburg-Wissenbach, all of Germany

[73] Assignee: Fritz Aurel Goergen, Cologny, Switzerland

[21] Appl. No.: 737,085

[22] Filed: Oct. 29, 1976

[30] Foreign Application Priority Data

Oct. 31, 1975 [DE] Fed. Rep. of Germany ....... 2548760

[51] Int. Cl.² .......................... F23G 5/02; F23G 5/04
[52] U.S. Cl. ................................. 110/220; 110/222; 110/224; 110/346
[58] Field of Search ............... 110/7 R, 8 R, 8 P, 8 F, 110/10, 14, 15, 18 R; 241/DIG. 38; 209/293, 296

[56] References Cited

U.S. PATENT DOCUMENTS

| | | | |
|---|---|---|---|
| 3,818,846 | 6/1974 | Reese | 110/8 |
| 3,848,813 | 11/1974 | Stanczyk | 241/DIG. 38 |
| 3,938,449 | 2/1976 | Frisz | 110/8 |
| 4,015,546 | 4/1977 | Paules | 110/10 |

OTHER PUBLICATIONS

Handbook of Solid Waste Disposal, Hagerty et al., 1975, pp. 298–299.

Primary Examiner—Kenneth W. Sprague
Attorney, Agent, or Firm—Michael J. Striker

[57] ABSTRACT

Any bundles in household refuse are broken up and this refuse is then coarsely comminuted with the broken up bundles, only the hard components of the refuse being comminuted with the light components merely being temporarily deformed between a pair of rollers having surface formations. Thereafter the coarsely comminuted refuse is separated by means of a drum-type sieve into a heavy fraction and a light fraction. The light fraction is finely comminuted into granules which are blown into a burning chamber in which they are suspended on a gas. The granules are combusted in this chamber to form a hot gas that is recirculated to sterilize and dry the heavy fraction and to dry the finely comminuted light fraction before its burning.

28 Claims, 13 Drawing Figures

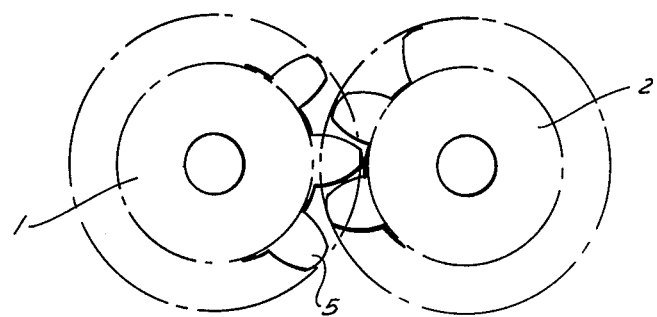
FIG. 3
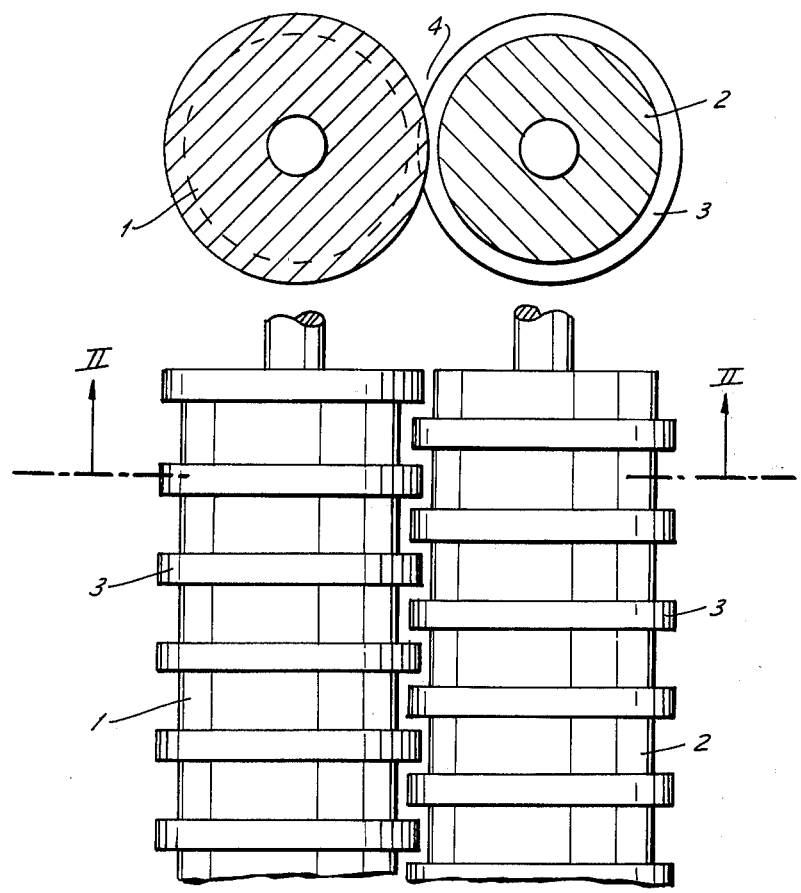
FIG. 2
FIG. 1

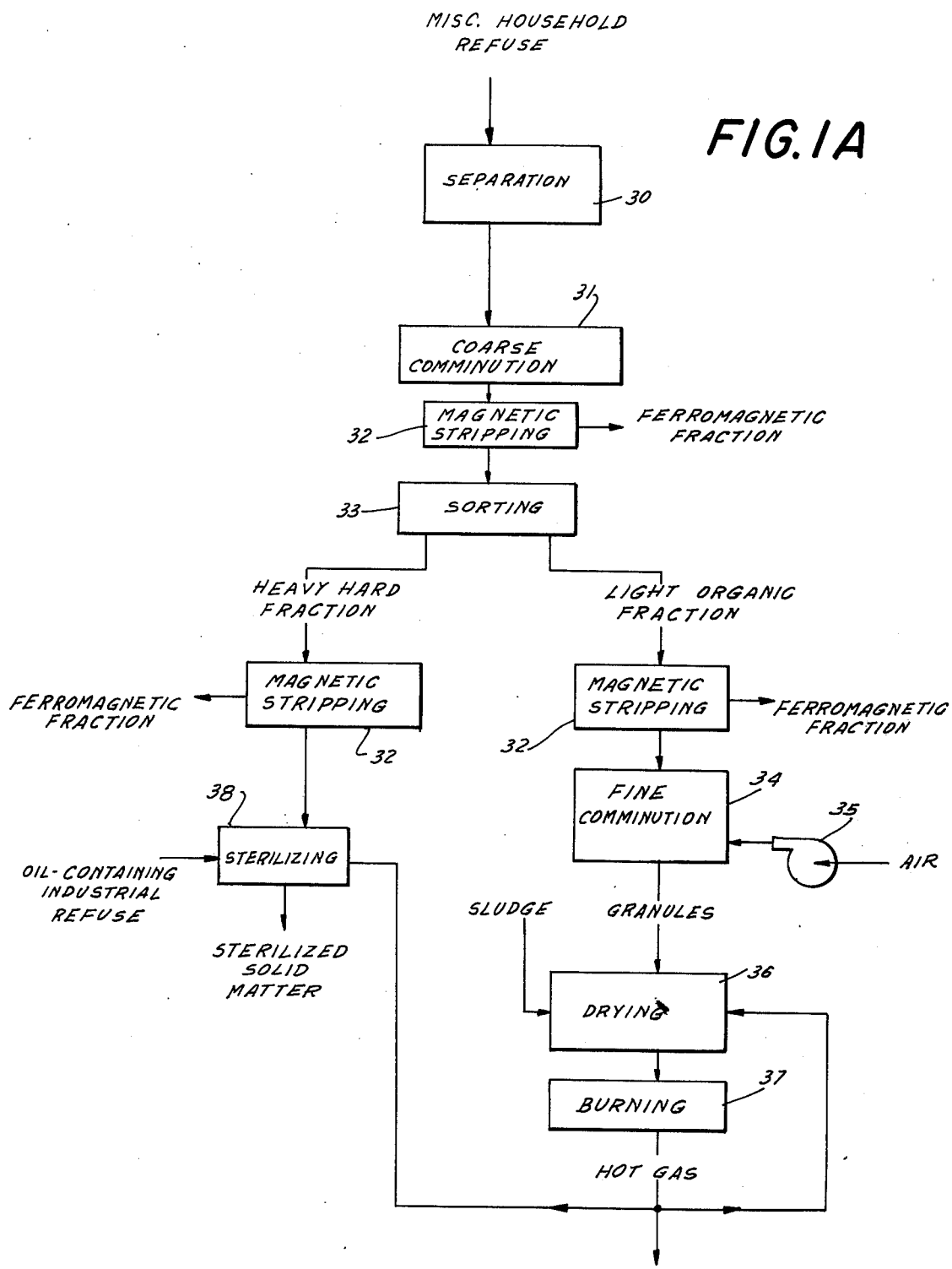

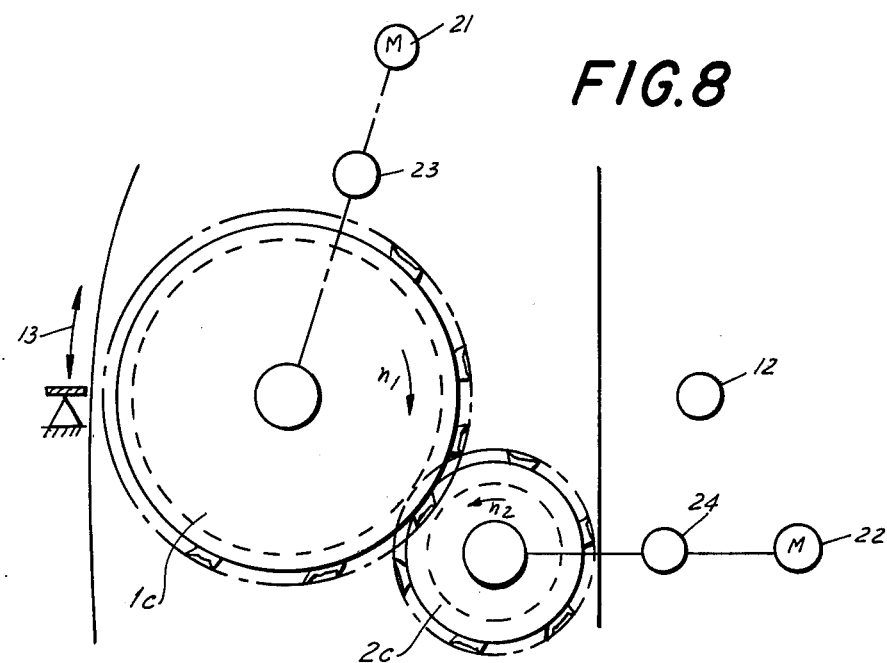
FIG. 8
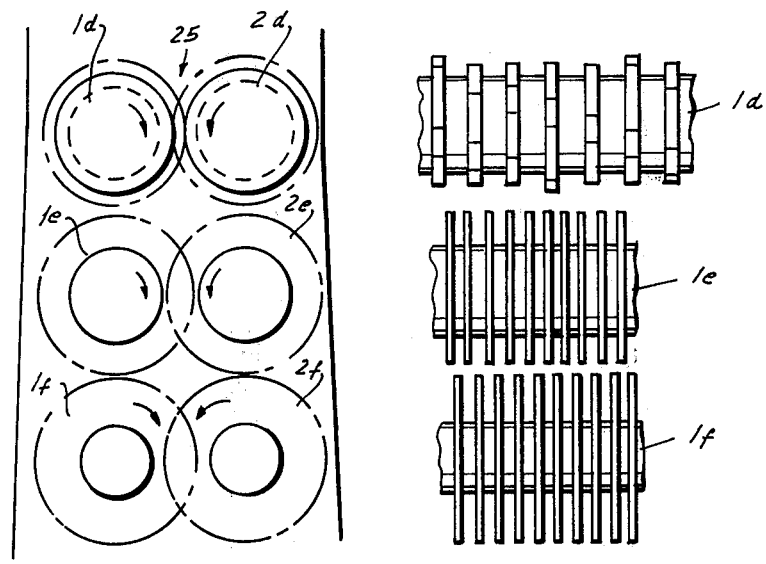
FIG. 9
FIG. 10

METHOD OF AND APPARATUS FOR TREATING REFUSE

BACKGROUND OF THE INVENTION

The present invention relates to a method of and an apparatus for treating refuse. More particularly this invention concerns a system for the nonpolluting disposal of refuse and the recovery of valuable recyclable constituents from refuse.

It is known to separate standard household refuse into a light organic fraction and a heavy hard fraction. This light fraction is comprised mainly of paper products, textiles, and the like and the heavy fraction is constituted of metal objects, stone, and otherwise very dense or wet objects. A common procedure is to comminute both fractions and feed the comminuted heavier fraction onto a grate in a combustion chamber. The comminuted light fraction is either blown directly or stored and then blown into the combustion chamber.

In such a system the principal combustion therefore takes place on the grate in the combustion chamber. The comminuted fine fraction which is blown in above the main fire on the grate is simultaneously combusted.

Such an arrangement has several disadvantages. First of all the grate tends to wear very rapidly, as it is subjected to considerable mechanical wear and considerable heat. In particular much refuse when burned produces corrosive acids which eat away even the most heavily constructed combustion grate. For this reason it is common practice in most such systems to provide several combustion chambers in parallel so that it is possible to shut one down at any given time and service it. Such servicing is required frequently and is expensive.

Furthermore, in such an arrangement the combustion of the refuse on the grate is often inadequate. The comminuted heavy fraction is frequently quite moist so that it cannot be burned completely. Thus, gases are produced which are themselves not sufficiently combusted so that it is necessary to provide a very expensive filtering arrangement at the outlet of this system in order to treat the noxious gases so produced.

In addition, such systems frequently are set up so that all of the refuse delivered to them must be treated immediately. Since it is common practice to use the heat created by such systems for the generation of electricity, it is therefore impossible to operate the systems at a higher rate during peak electricity-consumption hours.

It is also known in such systems to feed in wet sludge from a sewage-treatment installation. The intake rate of such sludge is normally dependent on the temperature in the combustion chamber, more sludge being fed in when the temperature is high and less when the temperature is low. Such an arrangement has the disadvantage that the wet sludge causes considerable generation of water vapor inside the combustion chamber. The water vapor combines with any acids driven out of the burning refuse so as to increase the pollution problem, and simultaneously increases the relative inertness of the atmosphere inside the combustion chamber. As the amount of water vapor increases the generation of carbon monoxide and other poisonous gases will also increse due to insufficient combustion, so that once again the system generates considerable pollution.

SUMMARY OF THE INVENTION

It is therefore an object of the present invention to provide an improved method of and apparatus for treating refuse.

These objects are attained according to the present invention in a method wherein refuse containing heavy and light components, bundles, and ferromagnetic articles is treated in six basic steps. First of all the bundles, by which is meant bagged refuse, newspaper tied up with string, and the like, is broken up. Secondly, all of the refuse including the broken-up bundles is coarsely comminuted into pieces at least one dimension of which is reduced to less than approximately 15 cm. Such coarse comminution therefore tends to have very little effect on the light or organic components constituting the light fraction of the trash or refuse, but does reduce the more solid parts of the refuse constituting the heavy or hard fraction. Thereafter the coarsely comminuted refuse with the broken up bundles is separated into a heavy fraction and a light fraction. As a fourth step, only the light fraction is finely comminuted into granules. These granules are blown into a burning chamber and are suspended on a gas in the chamber. Finally, the granules are combusted in the chamber so as to form a hot gas. Before or after the separation of the coarsely comminuted refuse into two fractions the refuse is stripped of ferromagnetic articles by means of an electromagnetic stripper including at least one magnet.

With the system according to the present invention the coarse comminution of the refuse leaves the light fraction containing the organic material such as paper, cardboard, textiles, plastic, and the like, virtually in its original state. The heavier fraction comprising the harder materials such as glass, ceramic, building material, and the like is either broken up or mashed into smaller pieces. Thus, it is possible to avoid the costly step of finely comminuting all of the refuse before processing it. In particular this is advantageous in that the comminution of the heavier or harder fraction of the refuse causes considerable wear in the comminution apparatus and a great consumption of energy.

In accordance with the present invention the lighter fraction is transformed into a coarse granulate. This is a relatively simple job since the light fraction normally is constituted by components which can readily be chopped, sheared, or torn into small parts. It is not necessary as has hitherto been the case to reduce the light fraction to a powdery state in order to ensure proper burning above the flame on the grate. It is also possible with such coarse granules to support combustion in the burning chamber without using a secondary burner or flame except to start up the operation.

In accordance with yet another feature of this invention at least some of the hot gas produced by the combustion of the granules is recirculated upstream and is used to dry the granules produced by the fine comminution so that they have less than 10% by weight of water. The thus-dried granules burn very readily. Such as arrangement clearly obviates the need for any type of support grate or the like in the combustion chamber so that this wear-prone part can be eliminated. The fire in the combustion chamber is comparable to that produced by wood chips or coal-dust, so that it is possible to use this system for the generation of electrical energy. Furthermore, it is possible to store the granulated and dried lighter fraction so that it can be burned during peak consumption hours for electricity.

The combustion chamber of a cyclone-type burning arrangement is much smaller in volume than the combustion chamber of a standard grate-type burning setup. It is therefore possible to work with a much higher combustion temperature which ensures excellent burning of the light fraction. Furthermore, such a high operating temperature considerably reduces the pollution produced by the arrangement and, therefore, makes the entire system much less expensive to operate.

In accordance with further features of this invention some of the hot gas produced by the combustion is recirculated and is used to pyrolyze the granules. This at least partially gasifies these granuls and greatly aids in the subsequent burning thereof. This once again makes it unnecessary to reduce the light fraction to a powder in order to obtain proper combustion. Furthermore, in accordance with this invention relatively flat components of the light fraction are reduced to a size of between 1.0 cm$^2$ and 3.0 cm$^2$ and lumpy or chunk-like components of the light fraction are reduced to a granulate or screen size of approximately 0.3 cm$^3$.

According to yet another feature of this invention sludge from a sewage-clarifying plant is dried along with the granules by means of the circulated hot gas from the combustion chamber, and is then fed with the granules into the combustion chamber. The drying of this sludge may take place at a location separate from the drying of the granules, but in either case the sludge is burned with the granules in the combustion chamber. Separate drying and storage of the sludge and granules is preferred in situations where it is necessary to vary the rate at which these are fed into the combustion chamber, as the combustibility of the sludge is substantially lower than that of the granules. The heat need of a boiler or the like that serves for the generation of electricity and is located downstream of the combustion chamber can determine the proportion of dried sludge to dried granules.

Furthermore, with such an arrangement the vapors produced by the drying of the sludge are also fed into the combustion chamber. This greatly reduces the pollution potential of the system, as these gases are normally rendered completely innocuous by combustion. In addition, the limited amount of dust which will inherently be picked up by surrounding gases when the sludge is dried is also fed into the chamber with these vapos so that it too is combusted and destroyed.

In accordance with yet another feature of this invention some of the hot gases produced in the combustion chamber are recirculated and employed to burn and/or sterilize the coarsely comminuted heavy fraction of the refuse. Such an arrangement also allows industrial refuse of a low heat value, often containing oil, to be added to the heavy fraction and sterilized with it. Such sterilization or burning can take place in a rotary drum or kiln which is heated by the gases from the combustion chamber of the system. Such heating has the effect of sterilizing this heavy fraction, since little burnable material is present in it. Nonetheless, the sifting or sorting according to this invention does leave enough burnable material in the heavy fraction so that it is not necessary to provide a large auxiliary burner or the like in the sterilizing apparatus as is required in any prior-art system.

In accordance with the present invention each of the comminutors comprises at least one pair of rolls having interengaging surface formations forming a gap through which the refuse is passed. The spacing between the formations of the coarse comminuter is substantially greater than that between the spacing of the fine comminuter, and the difference between peripheral speeds of the rolls of the coarse comminuter is much smaller than that between the rolls of the fine comminuter.

With this arrangement all of the refuse can be passed through the coarse comminuter, but only the heavy fraction is likely to be comminuted, as the light fraction will merely be mashed somewhat together as it passes between the rollers. Thus, the wear on the rollers is minimal with the heavier harder fraction being broken up into pieces smaller than 80 mm × 80 mm. When the sieve located downstream of this coarse comminuter is provided with perforations of approximately the same size, that is 80 mm on a side, only the coarsely comminuted heavy fraction will pass through this sieve, with the burnable light fraction remaining inside it.

At least one of the comminuters is provided with means for varying the rotational speed of at least one of its rolls. The peripheral speeds of the rolls of the coarse comminuter may be the same so that the difference between these speeds is equal to zero. As the difference between the peripheral speeds increases the tearing of the organic or light fraction is increased. Thus, the size reduction obtained is at least partially determined by the relative peripheral speeds.

In accordance with another feature of this invention the sieve used for sorting the light and heavy fractions is formed as a perforated cylindrical drum having and rotatable about a horizontal axis and provided internally with a horizontal auger which is juxtaposed with the lower portion of the drum and also rotated. The two elements are rotated relative to each other and the auger therefore moves material axially along the interior of the drum, while tossing components of the refuse up in the drum and causing all of the smaller components in the refuse to fall out through the above-mentioned holes in the drum. According to this invention the auger has a central large-diameter rod on which is provided an elastically deformable element extending helically and constituting a thread.

In accordance with yet another feature of this invention means is provided for scraping the inside of the drum as it turns. Such means may be formed as an axially extending endless belt having teeth or flaps which rub along the inside of the drum and strip from it refuse adhering to it. It is also possible to provide a rotary brush or scraper chain to clean the smooth cylindrical inside of the drum.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 1A is a flow chart illustrating the method according to the present invention;

FIG. 1 is a top view of a comminuter in accordance with this invention;

FIG. 2 is a section taken along line II—II of FIG. 1;

FIG. 3 is a view similar to FIG. 2 but illustrating an alternative form of the comminuter of this invention;

FIG. 8 is a vertical partly diagrammatic section through a comminuter according to the present invention;

FIG. 9 is a vertical diagrammatic section through yet another comminuter in accordance with this invention;

FIG. 10 is a side view of the comminuter shown in FIG. 9;

SPECIFIC DESCRIPTION OF PREFERRED EMBODIMENTS

Figure 5:
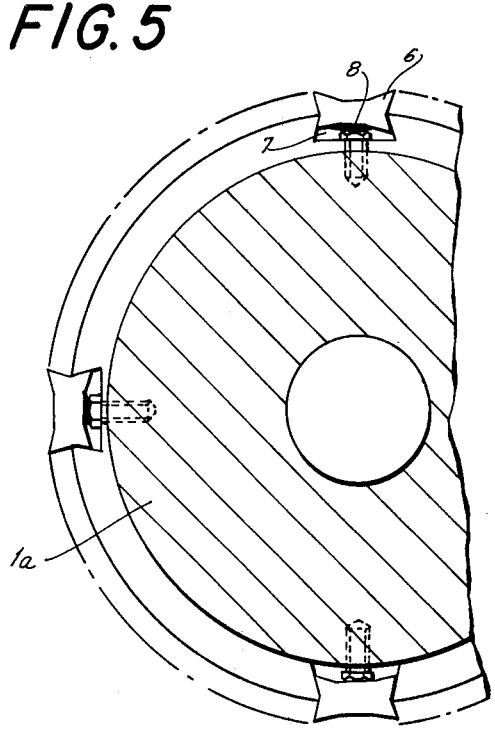
FIG. 5 is a section taken along line V—V of FIG. 4.

In accordance with the present invention as illustrated in FIG. 1A miscellaneous household refuse is first separated at 30, by which is meant the bundles, bags, and the like therein are broken up. Then it is subject at 31 to coarse comminution by apparatus described below. Thereafter it is magnetically stripped at 32 by means of an arrangement having at least one magnet, and of the type wherein, for instance, a rising belt underneath which a magnet is provided carries the refuse upwardly, with the nonferromagnetic fraction slipping downwardly but the ferromagnetic fraction being carried upwardly on the belt.

Thereafter the refuse is sorted at 33 by means of a sieve which is described below into a heavy or hard fraction and a light organic fraction. It is possible to then subject each of these fractions to a magnetic stripping at 32 instead of the earlier stripping.

The light organic fraction, which as been stripped of its ferromagnetic fraction either before or after the sorting at 33 is then subject to a fine comminution at 34. Air is blown in at 35 and the granules produced by the fine comminution at 34 are dried at 36. Thereafter the granules are blown into a combustion chamber 37 so as to produce a hot gas some of which is recirculated to the drier 36. It is also possible to feed sewage-treatment sludge into the drier 36, or to provide another drier 36 and a storage arrangement in parallel to the first-mentioned drier 36 for this sludge.

The heavy hard fraction if it has not already been magnetically stripped is stripped of its ferromagnetic fraction and is then sterilized at 38 with the help of some of the hot gas recirculated from the combustion chamber 37. It is also possible to add oil-containing industrial refuse to the coarsely comminuted heavy hard fraction in 38 in order to maximize the heat therein. Thus, the system produces sterilized solid matter and hot gas, with a minimum production of ash in the chamber 37.

As shown in FIGS. 1 and 2 the coarse comminution step 31 may be effected by means of a pair of rolls 1 and 2 having interengaging formations 3. Here these formations 3 are formed as square-section ridges extending above the cylindrical rolls 1 and 2 and lying in respective planes perpendicular to the axes of these rolls 1 and 2. The two rolls 1 and 2 therefore form a gap through which the refuse is passed.

It is also possible as shown in FIG. 3 to use axially extending formations 5 on the rolls 1 and 2 instead of the circumferential formations 3.

Figure 4:
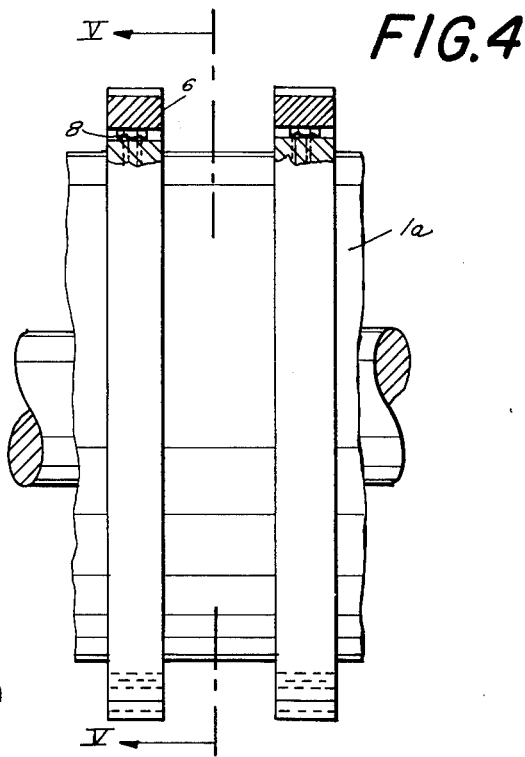
FIG. 4 is a side view partly in section illustrating a roller for a comminuter in accordance with this invention.

In the arrangement of FIGS. 4 and 5 a roller 1a is shown which is largely identical to the roller 1, but which is provided with teeth 6 held in dovetail-shaped grooves 7 and secured in place by means of screws 8. Each of these teeth 6 is completely symmetrical and doubly flared, so that it can fit into the dovetail groove 7 and be locked therein in any of four different positions by upwardly screwing the respective screw 8. These teeth 6 are made of hardened material and can readily be replaced or resurfaced.

Figure 7:
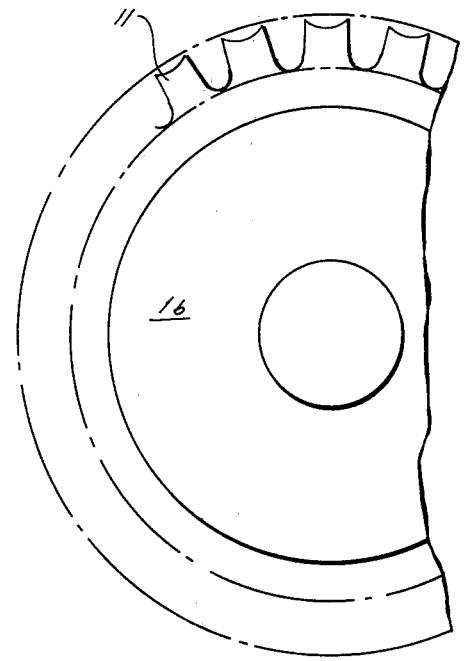
FIG. 7 is an end view of the roller shown in FIG. 6.
Figure 6:
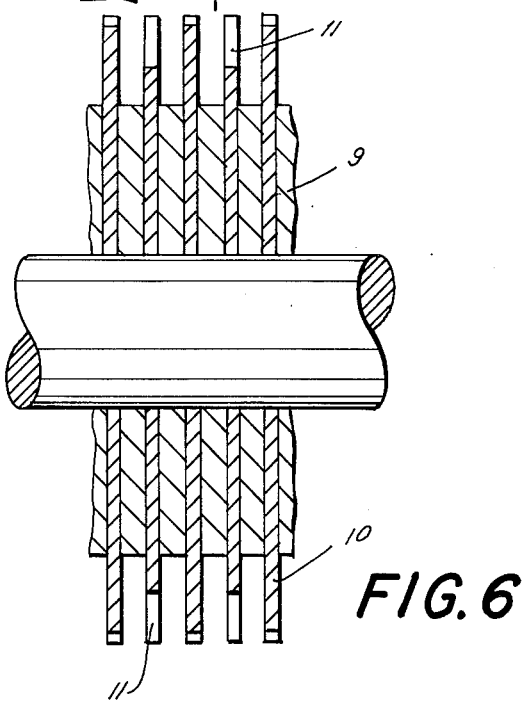
FIG. 6 is an axial section through a roller of yet another comminuter according to the present invention.

It is also possible as shown in FIGS. 6 and 7 to use a roller 1b constituted by a plurality of flat saw-like blades 10 separated by spacers 9 and each lying in a plane perpendicular to the axis of rotation for the roller 1b. Each of the blades 10 is circumferentially formed with a multiplicity of outwardly extending M-shaped teeth 11. This type of roller 1b is used for the fine comminution as illustrated at box 34 in FIG. 1A. It is also noted that the teeth 11 on adjacent blades 10 are so angularly offset relative to each other that a multiplicity of helically extending rows of teeth 11 are formed.

In FIG. 8 there is shown an arrangement wherein a large-diameter roller 1c and small-diameter roller 2c constructed as shown in FIG. 5 mesh with each other and are rotated by respective motors 21 and 22 through respective transmissions 23 and 24. The peripheral speed $n_2$ is equal to or greater than the speed $n_1$. Furthermore, the roller 1c is pivotal about a point and supportable on an abutment 13 so that in case the machine jams up this roller can jump up and allow the object jamming it to pass through. The motors 21 and 22 are hydrostatic.

The arrangement shown in FIGS. 9 and 10 has three sets of roller 1d, 2d; 1e, 2e; and 1f, 2f. They define a path 25 down through which the refuse may pass. Each roller rotates at a peripheral speed which forms a ratio with the peripheral speed of its mate equal to between 1 : 2 and 1 : 5. Furthermore, the peripheral speeds increase downwardly so that the ratio between the peripheral speeds of rollers 1d, 1e, and 1f is equal to between 1 : 2 : 3 and 1 : 1.5 : 2. What is more the uppermost rollers 1d and 2d are formed in substantially the manner shown in FIGS. 4 and 5 whereas the rollers 1e, 2e, 1f, and 2f are formed as shown in FIGS. 6 and 7.

Figure 11:
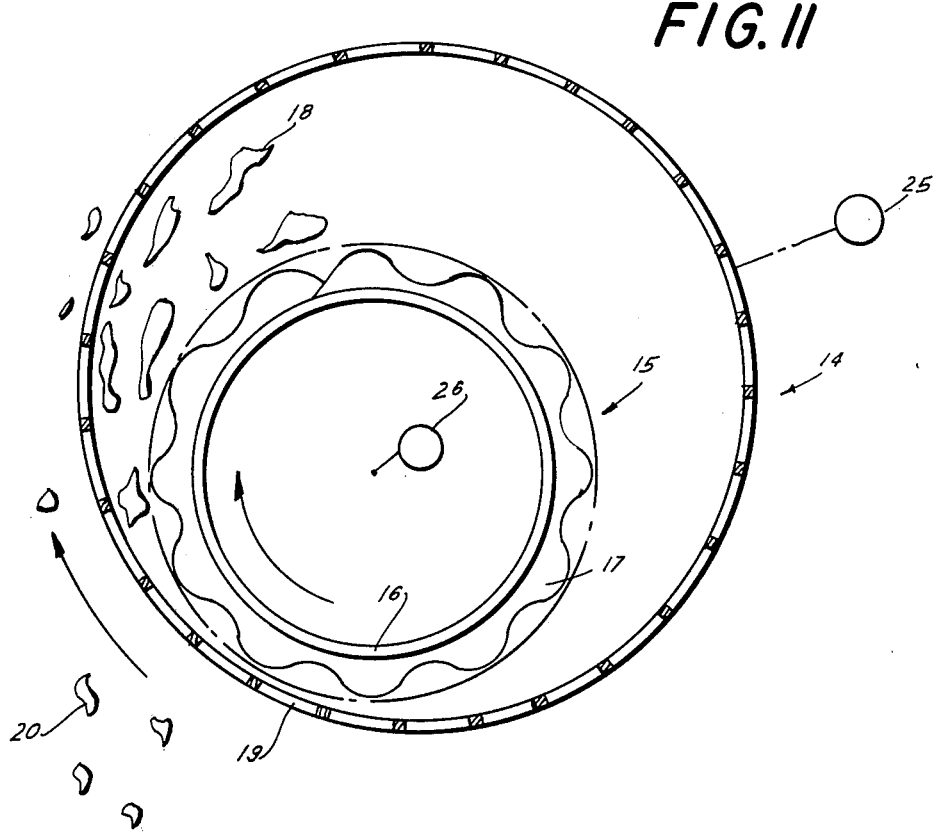
FIG. 11 is a cross section through a sieve in accordance with this invention.
Figure 12:
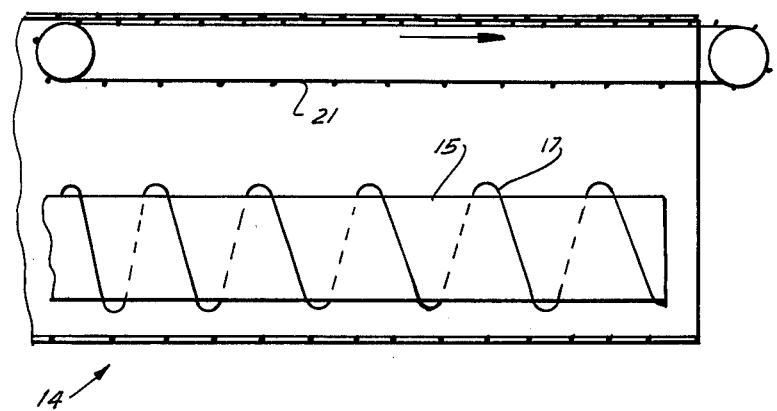
FIG. 12 is an axial section to the sieve of FIG. 11.

Finally, FIG. 11 shows a sieve usable at step 33 of this arrangement and comprising an outer cylindrical perforated drum 14 and an inner auger 15. The drum 14 has perforations 19, 80 mm on a side and the auger 15 is constituted as a central large-diameter tube 16 provided with a helically extending thread 17 formed of elastomeric material. The two elements are rotated about their respective axes by means of motors 26 and 27 so that trash or refuse 18 inside the drum 14 will be tossed upwardly, with the smaller parts 20 passing outwardly through the holes 19. FIG. 12 shows how a scraper belt 21 is provided to prevent the refuse from adhering to the smooth interior of the cylindrical drum 14.

A magnetic stripper such as used in step 32 can be seen in U.S. Pat. No. 2 213 668, the entire disclosure of which is herewith incorporated by reference. Similarly, a burning chamber such as used at 37 can be seen in German Offenlegungsschrift No. 23 59 730, also herewith incorporated by reference.

It will be understood that each of the elements described above, or two or more together, may also find a useful application in other types of systems differing from the types described above.

While the invention has been illustrated and described as embodied in a refuse-treating system it is not intended to be limited to the details shown, since various modifications and structural changes may be made without departing in any way from the spirit of the present invention.

Without further analysis, the foregoing will so fully reveal the gist of the present invention that others ca, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An apparatus for treating refuse containing heavy and light components, bundles and ferromagnetic articles, said apparatus comprising means for breaking up said bundles; a coarse comminuter including a pair of rolls rotatable about respective axes and formed with circumferential interengaging formations having a predetermined peripheral speeds differing by a predetermined difference for coarsely comminuting said refuse with the broken-up bundles; means including a sieve connected to said coarse comminuter for separating the coarsely comminuted refuse with the coarsely comminuted broken-up bundles into a heavy fraction and a light fraction, said sieve comprising an outer perforated cylindrical drum having and rotatable about a horizontal drum axis, an auger closely juxtaposed with and inside said drum and having and rotatable about an auger axis generally parallel to said drum axis and means connected to said drum and said auger for relatively rotating the same about their respective axes; a fine comminuter connected to said sieve and receiving only said light fraction, said fine comminuter including at least one pair of rolls rotatable about respective axes and formed with circumferential interengaging formations having a spacing smaller than said predetermined spacing and means for rotating said rolls of said fine comminuter at peripheral speeds differing by a difference greater than said predetermined difference for finaly comminuting said light fraction only into granules; a combustion chamber; means for blowing said granules into said chamber and for suspending said granules on a gas in said chamber; and means for combusting said granules in said chamber.

2. Apparatus for treating refuse containing heavy and light components, bundles and ferromagnetic articles, said apparatus comprising means for breaking up said bundles; a coarse comminuter for coarsely comminuting said refuse with the broken-up bundles; means including a sieve connected to said coarse comminuter for separating the coarsely comminuted refuse with the coarsely comminuted broken-up bundles into a heavy fraction and a light fraction, said sieve comprising an outer perforated cylindrical drum having and rotatable about a horizontal drum axis, an auger closely juxtaposed with and inside said drum and having and rotatable about an auger axis generally parallel to said drum axis and means connected to said drum and said auger for relatively rotating the same about their respective axes; a fine comminuter connected to said sieve and receiving only said light fraction for finely comminuting said light fraction only into granules; a combustion chamber receiving said granules for suspending said granules on a gas in said chamber; and means for combusting said granules in said chamber.

3. A method of treating refuse containing heavy and light components, bundles and ferromagnetic articles, said method comprising the steps of breaking up said bundles; thereafter coarsely comminuting said refuse with the broken-up bundles without substantial size reduction of said light components; thereafter separating the coarsely comminuted refuse with the brokenup bundles into a heavy fraction and a light fraction; finely comminuting only said light fraction into granules, sieving particles from said light fraction; thereafter drying said granules; blowing the dried granules into a burning chamber and suspending said dried granules on a gas in said chamber; and combusting said granules in said chamber while forming a hot gas.

4. The method defined in claim 3, further comprising the step of stripping from said refuse prior to step (d) said ferromagnetic articles.

5. The method defined in claim 4, further comprising the steps of recirculating said hot gas from step (g) over said granules during step e) to dry said granules with the recirculated hot gas to a moisture content of at most 10% by weight.

6. The method defined in claim 4, further comprising the steps of recirculating a portion of said hot gas from step (g) over said granules during step (e) and at least partially pyrolizing said granules with the recirculated hot gas.

7. The method defined in claim 4 wherein said light fraction is finely comminuted in step (d) by shearing.

8. The method defined in claim 4 wherein said light fraction is finely comminuted in step (d) by tearing.

9. The method defined in claim 4 wherein said light fraction includes flat components and lump components, the fine comminution of step (d) reducing said flat components to a size between 1 cm$^2$ and 3 cm$^2$ and reducing said lump components to a size of at most 0.3 cm$^3$.

10. The method defined in claim 3, further comprising the steps of drying sludge to produce dried sludge and vapors and thereafter feeding said dried sludge into said burning chamber for combustion thereof with said granules of step (d).

11. The method defined in claim 10, further comprising the step of feeding said vapors into said burning chamber and combusting means with said dried sludge and granules.

12. The method defined in claim 4, further comprising the step of recirculating a portion of said hot gas from step (g) and sterilizing the heavy fraction of step (c) therewith.

13. The method defined in claim 12, further comprising the step of mixing industrial waste containing oil with said heavy fraction prior to sterilization thereof.

14. The apparatus defined in claim 1, further comprising means including at least one magnet for stripping said ferromagnetic articles from said refuse before fine comminution of said light fraction.

15. The apparatus defined in claim 1 wherein at least one of said comminuters is provided with means for varying at least one of the respective peripheral speeds.

16. The apparatus defined in claim 1 wherein at least one of said comminuters has a plurality of such pairs of rolls defining a transport path and spaced apart by respective gaps decreasing along said path.

17. The apparatus defined in claim 1 wherein said formations of said fine comminuter are M-shaped teeth.

18. The apparatus defined in claim 17 wherein said rolls of said fine comminuter are each constituted as a plurality of planar blades bearing said teeth and spacers separating said blades axially.

19. The apparatus defined in claim 1 wherein said auger comprises an axially centered rod and a generally helically extending nonuniform formation thereon.

20. The apparatus defined in claim 19 wherein said formation of said auger is elastically deformable.

21. The apparatus defined in claim 1 wherein said means of said sieve rotates both said drum and said auger in the same rotational sense about their respective axes.

22. The apparatus defined in claim 1, wherein said sieve further comprising means for scraping adhered material from inside said drum.

23. The method defined in claim 3 wherein particles are smaller than a mesh size of 80 mm.

24. An apparatus for treating refuse containing heavy and light components, bundles, and ferromagnetic articles, said apparatus comprising:
  means for breaking up said bundles;
  means including a sieve for separating said refuse with the broken-up bundles into a heavy fraction and a light fraction, said sieve having
    an outer perforated cylindrical drum having and rotatable about a horizontal drum axis,
    an auger closely juxtaposed with and inside said drum and having and rotatable about an auger axis generally parallel to said drum axis, and
    means connected to said drum and said auger for relatively rotating same about their respective axes;
  a fine comminuter connected to said sieve and receiving only said light fraction, said fine comminuter including at least one pair of rolls rotatable about respective axes and formed with circumferential interengaging formations and means for rotating said rolls of said fine comminuter for finely comminuting said light fraction only into granules;
  a combustion chamber;
  means for blowing said granules into said chamber and for suspending said granules on a gas in said chamber; and
  means for combusting said granules in said chamber.

25. An apparatus for treating refuse containing heavy and light components, bundles, and ferromagnetic articles, said apparatus comprising:
  means for breaking up said bundles;
  a coarse comminuter including a pair of rolls rotatable about respective axes and formed with circumferential interengaging formations having a predetermined spacing and means for rotating said rolls at predetermined peripheral speeds differing by a predetermined difference for coarsely comminuting said refuse with the broken-up bundles;
  means including a sieve connected to said coarse comminuter for separating the coarsely comminuted refuse with the coarsely comminuted broken-up bundles into a heavy fraction and a light fraction, said sieve including
    an outer perforated cylindrical drum having and rotatable about a horizontal drum axis;
    an auger closely juxtaposed with and inside said drum and having and rotatable about an auger axis generally parallel to said drum axis, and
    means connected to said drum and said auger for relatively rotating same about their respective axes;
  a fine comminuter connected to said sieve and receiving only said light fraction, said fine comminuter including at least one pair of rolls rotatable about respective axes and formed with circumferential interengaging formations having a spacing smaller than said predetermined spacing and means for rotating said rolls or said fine comminuter at peripheral speeds differing by a difference greater than said predetermined difference for finely comminuting said light fraction only into granules;
  a combustion chamber;
  means for blowing said granules into said chamber and for suspending said granules on a gas in said chamber; and
  means for combusting said granules in said chamber.

26. A method of treating refuse containing heavy and light components, bundles, and ferromagnetic articles, said method comprising the steps of breaking up said bundles; thereafter coarsely comminuting said refuse with the broken up bundles; thereafter separating the coarsely comminuted refuse with the broken-up bundles into a heavy fraction and a light fraction; sieving particles from said light fraction; finely comminuting only said light fractions into granules; thereafter drying said granules; blowing the dried granules into a burning chamber and suspending said granules on a gas in said chamber; and combusting said granules in said chamber while forming a hot gas.

27. An apparatus for treating refuse containing heavy and light components, bundles, and particles, said apparatus comprising means for breaking up said bundles and coarsely comminuting said refuse without substantial size reduction of said light components; means for separating the coarsely comminuted refuse into a heavy fraction and a light fraction; means for separating said particles from said light fraction; means including a fine comminuter for receiving said light fraction and finely comminuting the same into granules larger than said particles; means for drying said granules; a combustion chamber; means for blowing said granules into said chamber and for suspending said granules on a gas in said chamber; and means for combusting said granules in said chamber.

28. An apparatus for treating refuse containing heavy and light components, bundles and particles, said apparatus comprising means for breaking up bundles and coarsely comminuting said refuse; means for separating the coarsely comminuted refuse into a heavy fraction and a light fraction; means for separating said particles from said light fraction; means including a fine comminuter for receiving said light fractions and finely comminuting the same into granules larger than said particles; means for drying said granules; means including a combustion chamber for receiving said granules and combusting said granules in said chamber.

* * * * *